(12) United States Patent
Edwards

(10) Patent No.: US 6,451,591 B1
(45) Date of Patent: Sep. 17, 2002

(54) DEVICE AND METHOD FOR THE DETERMINATION OF PROTEIN DOMAIN BOUNDARIES

(76) Inventor: Aled Edwards, 21 Sutherland Drive, Toronto, Ontario (CA), M4G 1H1

( * ) Notice: Subject to any disclaimer, the term of this patent is extended or adjusted under 35 U.S.C. 154(b) by 0 days.

(21) Appl. No.: 09/720,272

(22) PCT Filed: Jul. 15, 1999

(86) PCT No.: PCT/CA99/00640
§ 371 (c)(1),
(2), (4) Date: Mar. 12, 2001

(87) PCT Pub. No.: WO00/04384
PCT Pub. Date: Jan. 27, 2000

(30) Foreign Application Priority Data

Jul. 15, 1998 (CA) .......................................... 2243230

(51) Int. Cl.⁷ ................................................. C12M 1/22
(52) U.S. Cl. ............................. 435/305.2; 435/288.4; 435/970; 435/975; 435/23; 422/102
(58) Field of Search ........................ 435/287.7, 288.4, 435/305.2, 970, 975, 4, 7.9, 7.91, 23; 422/102

(56) References Cited

U.S. PATENT DOCUMENTS

| | | | |
|---|---|---|---|
| 3,519,538 A | | 7/1970 | Messing et al. |
| 3,556,945 A | | 1/1971 | Messing |
| 3,666,627 A | | 5/1972 | Messing |
| 3,802,997 A | | 4/1974 | Messing |
| 4,146,432 A | | 3/1979 | Hirohara et al. |
| 5,856,082 A | * | 1/1999 | Aebersold et al. ............. 435/4 |
| 6,221,626 B1 | * | 4/2001 | Bienvenut et al. ............ 435/23 |

FOREIGN PATENT DOCUMENTS

DE 44 03 057 12/1994

OTHER PUBLICATIONS

Barwell et al. (1995), *Overexpression, Purification, and Crystallization of the DNA Binding and Dimerization Do,mains of the Epstein–Barr Virus Nuclear Antigen 1*, J. Biol. Chem. 270(35):20556.

Malhotra et al. (1996), *Crystal Structure of a $\sigma^{70}$ Subunit Fragment from E. Coli RNA Polymerase*, Cell 87:127.

Chibata (1978), *Immobilized Enzymes*, Halstead Press.

Zaborsky (1973), *Immobilized Enzymes*, CRC Press.

Márquez et al.; "Quantitative Analysis of Exogenous Peptides in Plasma Using Immobilized Enzyme Cleavage and Gas Chromatography Mass Spectrometry with Negative Ion Chemical Ionization", Journal of Chromatography B, 700: 9–12, (1997).

Milenic et al.; "Comparison of Methods for the Generation of Immunoreactive Fragments of a Monoclonal Antibody (B72.3) Reactive with Human Carcimonas", Journal of Immunological Methods 120:71–83, (1989).

Morin et al.; "Elongation Factor TFIIS Contains Three Structural Domains: Solution Structure of Domains II", Proc. Natl. Acad. Sci. USA vol. 93: 10604–10608, ( Oct. 1996).

Pfuetzner et al.; "Replication Protein A: Characterization and Crystallization of the DNA Binding Domain", The Journal of Biological Chemistry, 272(1): 430–434, (Jan. 3, 1997).

International Search Report Completed on Nov. 11, 1999 and Mailed on Nov. 24, 1999.

* cited by examiner

Primary Examiner—David A. Redding
(74) Attorney, Agent, or Firm—Foley Hoag LLP; Kingsley L. Taft; Isabelle M. Clauss

(57) ABSTRACT

A method and device to assist in the determination of protein domain boundaries is described. In particular the device is designed to provide a high throughput of proteolytic digestion of proteins to identify domains and their boundaries, for use in protein structure determination, in a manner that is amenable to automation. Proteases are immobilized in a convenient format such as a microtitre plate and preferably arranged in a matrix thereby allowing for simultaneous degradation of a protein by a number of proteases at a number of concentrations.

17 Claims, 2 Drawing Sheets

DEVICE AND METHOD FOR THE DETERMINATION OF PROTEIN DOMAIN BOUNDARIES

FIELD OF INVENTION

The present invention generally relates to methods for determination of protein structure and in particular concerns the use of immobilized proteases to identify domain boundaries of proteins, and an apparatus for digesting proteins.

BACKGROUND OF INVENTION

The molecular structure of proteins allows them play crucial roles in virtually all biological processes, including: enzymatic catalysis, transport and storage; coordinated motion; mechanical support; immune protection; generation and transmission of nerve impulses; and control of growth and differentiation. In particular, the side chains of the different amino acids that comprise proteins, enables these long macromolecules to fold into distinctive structures and form complementary surfaces and clefts and enables them to specifically recognize and interact with highly diverse molecules. The catalytic power of enzymes comes from their capacity to bind substrates in precise orientations and to stabilize transition states in the making and breaking of chemical bonds. Conformational changes transmitted between distant sites in protein molecules are at the heart of the capacity of proteins to transduce energy and information. Thus, the three dimensional structure of a protein is the key to its ability to function in virtually all biological processes.

Discussions pertaining to protein architecture concern four levels of structure which are described as follows. Primary structure is the amino acid sequence. Secondary structure refers to the spatial arrangement of amino acid residues that are near one another in the linear sequence. Some of these steric relationships are of a regular kind, giving rise to a periodic structure. Tertiary structure refers to the spatial arrangement of amino acid residues that are far apart in the linear sequence, and to the pattern of disulfide bonds. The term, quaternary structure, refers to proteins containing more than one polypeptide chain where each polypeptide chain is referred to as a subunit, and the quaternary structure refers to the spatial arrangement subunits and the nature of their contacts.

Some polypeptide chains fold into two or more compact regions that may be joined by a flexible segment of polypeptide chain. These compact globular units, called domains, range in size from about 50 to 400 amino acid residues, and they seem to be the modular units from which proteins are constructed. While small proteins may contain only a single domain, larger proteins contain a number of domains, which are often connected by relatively open lengths of polypeptide chain. Although all information required for folding a protein chain is contained in the protein's amino acid sequence, it is not yet known how to "read" this information so as to predict the detailed three-dimensional structure of a protein whose sequence is known. Consequently, folded conformation currently can only be determined by an elaborate X-ray diffraction analysis performed on crystals of the protein or, if the protein is very small, by nuclear magnetic resonance ("NMR") techniques. Although considerable advances are being made in the area of high field NMR, presently, the only method capable of producing a highly accurate three dimensional structure of most proteins is by the application of X-ray crystallography.

Recent advances in the field of X-ray crystallography, such as high speed computer graphics and X-ray area detection technologies, have revolutionized the pace at which three-dimensional structures can be determined. The resulting three dimensional structure produced from the protein crystals can have enormous implications in the fundamental understanding of molecular biology such as how enzymes perform various catalytic activities, switch on biological pathways, or transport molecules within the circulatory system. In the past few years the determination of protein structures important as therapeutic targets has made possible the rational design of new, more effective pharmaceuticals.

The technique of X-ray crystallography utilizes the diffraction of X-rays from crystals in order to determine the precise arrangement of atoms within the crystal. The limiting step in the technique involves the growth of a suitable crystalline sample. This requires the growth of reasonably ordered protein crystals (crystals which diffract X-rays to at least 3.0 angstroms resolution or less).

Because of the complexity of proteins, obtaining suitable crystals can be quite difficult. Typically, several hundred to several thousand individual experiments must be performed to determine crystallization conditions, each examining a matrix of pH, buffer type, precipitant type, protein concentration, temperature, etc. This process is extremely time consuming and labour intensive.

A strategic approach has been developed to identify protein domains that are amenable to NMR analysis or X-ray crystallography. Different domains of a protein may be linked together by intervening sections of polypeptide chain to form the protein molecule. Analysis of a single domain is more easily conducted in isolation from its parent protein. The determination of an individual domain structure facilitates elucidation of the parent structure. Limited proteolysis has been used to isolate and identify stable domains of proteins, which have a high likelihood of being good targets for protein structure determination. The approach is based upon the observation that low concentrations of one or more specifically chosen proteases cleave proteins into proteolytically stable domains amenable to NMR analysis or crystallography (Morin, P. E.; et aL Proc. And. Acad. Sci. 1996, 93, 10604–10608; Barswell, J. A.; et al. J. Bio. Chem. 1995, 270, 20556–20559; Pfuetzner, R. A.; et al. J. Bio. Chem. 1997, 272, 430–434; and Malhotra, A; el aL Cell 1996, 87, 127–136).

Limited proteolysis has been conducted to isolate and identify stable domains of proteins. Generally, according to this process, the protein is incubated with four to six different proteases at different concentrations for different amounts of time. Typical protease digestion reactions are conducted by dissolving an enzyme in water thereby allowing the enzyme to act on a substrate in an aqueous solution. However, the fact that the enzyme reaction is a homogeneous reaction in an aqueous solution is a great hindrance to performance of a continuous reaction in industrial applications and also makes it very difficult to recover remaining active enzymes for repeated use after the reaction. In addition, complicated operational procedures are necessary for separation and purification of the reaction product.

The digestion products can be analyzed by SDS/polyacrylamide gel electrophoresis and proteolytically stable fragments can be identified on the basis of approximate mass. These products can then be isolated by reverse phase chromatography and an accurate mass determination can be performed by mass spectrometry. The accurate mass of a proteolytic fragment is sufficient to uniquely identify the boundaries of the fragment within a sequence of a protein.

The identification of the proteolytic fragment sequence facilitates the recombinant preparation of the domain in sufficient quantities for X-ray and NMR analysis.

A limitation of the aforementioned strategy is the time consuming nature of cleaving, identifying and isolating the domains of a protein from the digestion solution.

SUMMARY OF THE INVENTION

The present invention provides a method and device to assist in the determination of protein domain boundaries. In accordance with an aspect of the invention there is provided a method for the preparation of proteolytically digested fragments of a protein in one step for purification and further processing for determination of domains and their boundaries in the protein, The method developed by present inventor comprises a one step degradation of protein which comprises contacting a quantity of the protein with two or more concentrations of one or more immobilized proteases for a time sufficient to allow degradation of the protein to provide digested fragments and then separating the immobilized protease from the fragments. Each protease is immobilized in a compartment in an apparatus which comprises a plurality of compartments, each compartment containing a quantity of a protease immobilized on a surface in each compartment. According to a preferred embodiment each compartment contains a concentration of the protease distinct from the concentration of the protease in every other compartment. Preferably the surface upon which the protease is immobilized has been treated with a blocker of surface interaction. The protein is contacted with the protease in each compartment at about the same time.

In accordance with a further aspect of the invention the method is automated allowing for simultaneous addition of a quantity of the protein to each of the compartments. Downstream automation removes protolytically treated fragments to a purification step to yield one or more samples for further processing and structure determination. Accordingly, the present invention provides a high throughput method and device for enzymatically cleaving proteins into domains which allows for an efficient means to identify protein domain boundaries for use in protein crystallization, in a manner that is amenable to automation.

In accordance with one aspect of the present invention a device of the invention is connected downstream to an automatic means of adding a protein solution, or a solution of a protein fragment, and upstream to an automatic means of removing and subjecting the proteolytically digested product to a purification step.

In accordance with another aspect of the present invention there is provided a method for determining the boundaries of a proteolytically digested fragment of a protein which comprises the steps: (i) incubating a protein, or a fragment thereof, with at least one immobilized protease to yield protein fragments; and (ii) subjecting the resulting protein fragments to one or more purification steps to isolate the fragments of interest; (iii) subjecting the isolated fragment (s) to either nanospray or matrix-assisted time-of-flight mass spectrometry; (iv) matching the mass of the proteolytic fragment to the protein sequence of the protein originally digested.

According to another aspect of the present invention there is provided an apparatus for degradation of a protein, where the apparatus comprises a plurality of compartments, with at least two different concentrations of protease in separate compartments. In a preferred embodiment each compartment contains a concentration of protease distinct from the concentration of protease in every other compartment.

The present invention also includes a kit containing the device of the present invention together with appropriate reagents and instructions for its use.

Once proteins domains have been determined by the methods of the present invention, these protein domains can be used in screens of protein-protein interaction, such as for example, by affinity chromatography.

Advantages of the present invention include the primary factor that proteases and protease fragments do not substantially contaminate the proteolytically digested protein fragments as the proteases are immobilized and not in solution.

Another advantage is the ability to re-use the treated plates. Another advantage is the reproducibility and as mentioned, high throughput of protease digestion.

Because many devices can be generated at the same time, there is an efficiency of production and consistency of immobilized protease concentration that can be attained by this invention that is not currently available in the art. Some of the plates with an immobilized protease can be mass produced and stored for at least one week, at 4° C., while maintaining activity. Plates can be manufactured as standards or as custom models as requested.

In contrast to autolytic proteases (and mixtures of proteases that can degrade due to one protease cleaving another protease, in solution), the ready use format of the present invention provides an immobilized product that: (1) is essentially unable to undergo autolytic cleavage; and (2) is essentially unable to degrade due to one protease cleaving another protease.

DETAILED DESCRIPTION OF THE INVENTION

Figure 1:
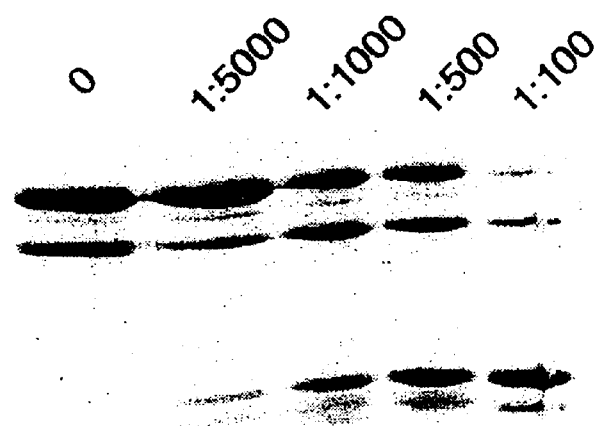
FIG. 1 shows a comparison of PAGE results of a limited digestion of the transcription factor TFIIS from the yeast, *Saccharomyces cerevisiae*. in solution and in microtitre plates.
Figure 1:
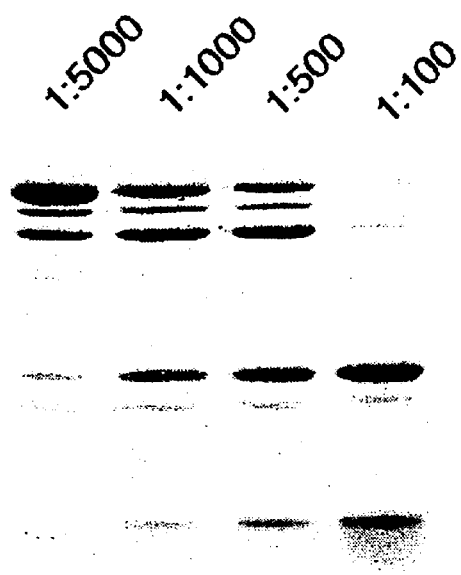

Current limitations in the art of identifying stable domains of proteins for use in structure determination are overcome by use of this invention which provides a device and method for conducting limited proteolysis of proteins to identify protein domains useful for structure determination. In particular the device is designed to provide a high throughput of proteolytic digestion of proteins to identify domains and their boundaries, for use in protein structure determination, in a manner that is amenable to automation.

As used herein the word "protein" includes the terms "peptide" and "polypeptide" and includes a fragment of a protein as well as an amino acid chain which provides a fully constituted molecular structure such as the transcription factor TFIIS from the yeast, *Saccharomyces cerevisiae*.

As used herein, the phrase "proteolytically digested protein" means the degradation of a protein by an enzyme or protease and includes limited degradation of a protein by an enzyme or protease.

As used herein the phrase "solid support" includes any substance which is capable of interacting with a protease or other enzyme and holding it out of solution, and includes for examples organic and inorganic support materials as described herein.

As used herein "compartment" includes any structure which is capable of supporting an immobilized protease, for example, a well in a microtitre plate, a column containing a resin or other bead-like particle. It will be understood that there may be duplicates and triplicates of some concentrations within a plurality of compartments of an apparatus of the invention, so long as over all there are at least two or three different concentrations. Further, it is understood that a number of apparatuses of the invention may be used in parallel to create a super matrix with numerous repeats of a particular concentration all within one apparatus with each apparatus having differing concentrations of protease.

Method of the Invention

The present invention provides a method for the preparation of proteolytically digested fragments of a protein, free of protease, for the determination of domains and the boundaries of the domains in said protein, the method comprises:

(1) contacting a quantity of the protein with at least two concentrations of a protease under conditions which result in digested fragments of the protein, wherein each of the concentrations of protease is immobilized in a separate compartment; and (2) separating said fragments from the immobilized protease. Preferably the compartment is in an apparatus which comprises a plurality of compartments.

According to one embodiment of the method compartment containing a quantity of the protease contains a concentration of the protease different from the concentration of the protease in every other compartment. Preferably at least three concentrations of protease are in at least three different compartments.

According to another embodiment the plurality of compartments forms a matrix in a linear format with at least three increasing concentrations of protease in the compartments. Preferably the matrix contains more than one protease.

According to a preferred embodiment of the method the compartments form a matrix in a two-dimensional format wherein: (i) distinct concentrations of each protease are aligned in increasing concentration, along a first axis or concentration axis; and (ii) different proteases are aligned along a second axis that is perpendicular to the first axis.

A protease for use in ta method of the invention is selected from the group consisting of aminopeptidase M; bromelain; carboxypeptidase A, B and Y; chymopapain; chymotrypsin; clostripain; collagenase; elastase; endoproteinase Arg-C, Glu-C and LysC; Factor Xa; ficin; Gelatinase; kallikrein; metalloendopeptinidase; papain; pepsin; plasmin; plasminogen; peptidase; pronase; proteinase A; proteinase K; subsilisin; thermolysin; thrombin; and trypsin. Preferably the proteases are trypsin, chymotrypsin, proteinase K or papain.

According to a preferred embodiment the concentrations of each of the proteases along the first axis in each case is from about 50 µg/mL to about 0.5 µg/mL. More preferably the concentration for each of the proteases is about 50 µg/mL in one container of a concentration axis; about 25 µg/mL in a second container of the concentration axis; about 5 µg/mL in a third container of the concentration axis; about 2.5 µg/mL in a fourth container of the concentration axis; about 0.5 µg/mL in a fifth container of the concentration axis; about 0 µg/mL in a sixth container of the concentration axis.

A preferred embodiment of the method requires that the surface upon which the protease is immobilized has been treated with a blocker of surface interaction. Preferably the blocker is selected from the group consisting of BSA and beta-octyl glucoside.

According to another aspect of the method the surface to which the protease(s) is/are immobilized is selected from the group consisting of an organic support of material selected from the group consisting of polyesters, polyamides, polyacrylates, polymethacrylates, polyacrylamides, poly (acrylic acid)m, poly(methacrylic acid); poly(galacturonic acid); poly(aspartic acid); ethylene-maleic anhydride copolymers; polyolefins; cellulose; cellulose derivatives; agarose gels; dextran gels and derivatives thereof, polysaccharides; polypeptides; collagen; and an inorganic support material selected from the group consisting of siliceous and nonsiliceous metal oxides.

In a preferred embodiment of the method the apparatus is a microtitre plate and the time for incubation of protein with immobilized protease is between about 2 to 4 hours. Preferably the temperature for the reaction between immobilized protease and protein is room temperature. According one embodiment of the method only limited digestion of the protein occurs.

Accordingly carrying out the method of the present invention provides proteolytically digested protein fragments substantially free of digesting protease by using proteases that are immobilized on a solid support such as a microtiter well. Coupling of the immobilized protease plates to a chromatographic step for separation of the protein fragments thereby generated, prepares the fragments for further analysis such as sequence determination or mass spectrometry. The design of the device allows for a high throughput of protein samples in addition to being particularly suitable for automation. As such the present invention provides a method for determining the boundaries of a proteolytically digested fragment of a protein which comprises the steps: (i) incubating a protein, according to the methods described herein to yield protein fragments; (ii) isolatation of fragment(s) of interest; (iii) determining the mass of the isolated fragment(s); and (iv) matching the mass of the proteolytic fragment(s) to a protein amino acid sequence of the protein digested. Preferably the determination of mass is by a method selected from the group consisting of nanospray time-of-flight mass spectrometry and matrix-assisted time-of-flight mass spectrometry. Also, preferably the protein fragment isolation is carried out by a technique selected from the group consisting of High Performance Liquid Chromatograph (HPLC) and sodium dodecylsulphate (SDS) polyacrylamide gel electrophoresis (PAGE). The loading and transference of the protein samples to the device and, following the reaction, to a detector such as HPLC or mass spectrometer, can be performed by automated means known in the art. According to a preferred embodiment the method is automated.

Automated sampling and automated transfer and mixing of solutions and solvents is routine. Many commercial automated apparatuses are available and save considerable hours and days of sample manipulation. For example, auto samplers for HPLC, gas chromatography and mass spectrometry are all commercially available. In addition, commercial solution handling devices are readily customised to suit the users needs. The employment of such automated handlers in conjunction with protease immobilized plates removes the steps of manipulating a protease solution and subsequent removal of unwanted protease reagent and protease fragments.

The use of the protease plates allows highly parallel domain mapping. The plates, with commercially available robotics, can be coupled with HPLC and mass spectrometry to make an integrated system for the rapid molecular identification of protein domains.

Apparatus of the Invention

An apparatus of the present invention can be used to treat a protein solution containing whole proteins or fragments thereof to limited proteolysis to generate stable domains of the proteins for further analysis. Accordingly the present invention provides an apparatus for degradation of a protein, where the apparatus comprises a plurality of compartments, each compartment containing a quantity of a protease immobilized on a surface in each compartment wherein at least two compartments contain different concentrations of the protease. Preferrably each of the compartments of the apparatus contain a concentration of the protease different from the concentration of the protease in every other compartment.

According to a preferred embodiment an apparatus according to the present invention contains at least three concentrations of protease in three compartments. Preferably a plurality of compartments forms a matrix in a linear format with at least three increasing concentrations of protease in at least three of the compartments. More preferably the apparatus contains more than one protease.

According to another embodiment of an apparatus of the present invention a plurality of compartments forms a matrix in a two-dimensional format wherein: (i) distinct concentrations of each protease are aligned in increasing concentration, along a first axis or concentration axis; and (ii) different proteases are aligned along a second axis that is perpendicular to the first axis.

According to a preferred embodiment an apparatus according to the present invention is a microtitre plate. A "microtitre plate" as referred to herein is well known to those skilled in the art and is a sample plate having one or more wells for receipt of a sample, the microtitre plate being suitable for use in an automated process. A plate well within a single microtitre plate can contain one or more proteases at a single concentration or differing concentrations or be a control blank. Due to the open layout of the microtiter wells, and the matrix of proteolytic enzymes, the design of the device permits a high throughput level of protein treatment that significantly diminishes the time required for an equivalent digestion procedure that is familiar in the art. Typically, such plates contain 96 wells, but higher volume plates such as 380 or more are also contemplated to function in the present invention.

On such microtitre plates a protease digestion matrix is generated with different proteases along one axis and increasing concentrations along the other axis.

Different proteases can be used, both alkaline and acidic. Moreover, given the existence of a multitude of known proteases and the application of recombinant DNA technology to the study and production of protease analogs, the art has yet to develop completely. Many proteases are available and can be used in this device and procedure, for example: aminopeptidase M; bromelain; carboxypeptidase A, B and Y; chymopapain; chymotrypsin; clostripain; collagenase; elastase; endoproteinase Arg-C, Glu-C and LysC; Factor Xa; ficin; Gelatinase; kallikrein; metalloendopeptinidase; papain; pepsin; plasmin; plasminogen; peptidase; pronase; proteinase A; proteinase K; subsilisin; thermolysin; thrombin; and trypsin. Preferably the proteases are trypsin, chymotrypsin, proteinase K or papain.

The larger the number of proteases with different specificity, the greater the procedural flexibility provided by one or more microtitre plates. In a preferred embodiment a single plate has six or more different immobilized proteases. Each protease is dispensed along a single row, with the concentration in the first well at 50 micrograms per millilitre and each subsequent well with a two-fold dilution. According to a preferred embodiment an apparatus according to the present invention has concentrations of each of the proteases along the first axis from about 50 $\mu$g/mL to about 0.5 $\mu$g/mL. More preferably the concentration for each of the proteases is about 50 $\mu$g/mL in one container of a concentration axis; about 25 $\mu$g/mL in a second container of the concentration axis; about 5 $\mu$g/mL in a third container of the concentration axis; about 2.5 $\mu$g/mL in a fourth container of the concentration axis; about 0.5 $\mu$g/mL in a fifth container of the concentration axis; about 0 $\mu$g/mL in a sixth container of the concentration axis. Preferably the surface upon which the protease(s) is are immobilized has been treated with a blocker of surface interaction where the blocker is selected from the group consisting of BSA and beta-octyl glucoside.

An apparatus of the invention can be stored for a period of at least a week, at 4° C. Preferably before storage the apparatus is lyophilized.

Immobilization of the enzyme on the solid support is readily accomplished by various methods which are known. Various methods are known for immobilization of enzymes (refer to, for example, O.R. Zaborsky, "Immobilized Enzymes", C.R.C. Press, 1973; or "Immobilized Enzymes", edited by Ichiro Chihata, Kodansha, 1975; see also see I. Chibata, Editor, "Immobilized Enzymes", Halsted Press, John Wiley & Sons, Inc., New York, 1978, pp. 1–73). They can roughly be classified into the following four groups: (1) physical or ionic adsorption method; (2) covalent attachment method; (3) entrapment method; and (4) crosslinking method.

In a preferred embodiment, the device is generated by immobilizing the proteases by overnight incubation at room temperature.

The solid support generally can be either organic or inorganic. Examples of organic supports include, among others, polyesters, such as poly(ethylene terephthalate); polyamides, such as nylon 6 and nylon 6.6; polyacrylates; polymethacrylates; polyacrylamides; poly(acrylic acid); poly(methacrylic acid); poly(galacturonic acid); poly (aspartic acid); ethylene-maleic anhydride copolymers; polyolefins, such as polyethylene, polypropylene, polybutene, and polybutadiene; polystyrene; poly (aminostyrene); poly(vinyl chloride); poly(vinyl alcohol); poly(vinylidene chloride); cellulose and derivatives thereof; agarose gels; dextran gels and derivatives thereof, polysaccharides; polypeptides; collagen; and the like.

The inorganic supports can be classified as siliceous or nonsiliceous metal oxides. Examples of siliceous supports include, among others, glass, silica, wollastonite, bentonite, cordierite, and the like. Examples of nonsiliceous metal oxides include, among others, alumina, spinel, apatite, nickel oxide, titania, zirconia, and the like.

In general, the support can be in any desired shape or form that is a continuous, shaped article such as a flat or curved sheet or a three-dimensional article such as a rectangular or cylindrical tube. As a practical matter, however, the support most often will be a microtiter plate or a similar shaped support.

For examples of procedures for immobilizing enzymes on inorganic supports, by way of illustration only, see U.S. Pat. No. 3,519,538 (which corresponds with French Patent No. 2,020,527), U.S. Pat. No. 3,556,945 (which corresponds with French Patent No. 2,001,336), and U.S. Pat. Nos. 3,666,627 and 3,802,997 (which correspond with French Patent No. 2,020,661).

In a preferred embodiment, the non-specific binding sites on the microtitre wells are blocked for a period of time (three hours) with an appropriate blocking solution containing 0.1% betaoctylglucoside, although depending upon the support material chosen other blockers will be preferred, such as for example bovine serum albumin (BSA).

Kit

In another embodiment, the present invention relates to a kit for conducting limited proteolysis digestion of proteins or protein fragments for structure determination analysis comprising at least one container including the above-described device. The proteolysis device can be presented in a commercially packaged form, a packaged combination of one or more containers, devices, or the like, holding the necessary reagents and usually including written instructions describing the performance of the digestion procedure. Reagent systems of the present invention involve all possible configurations and compositions for performing the various digestion formats described herein.

In a preferred embodiment, the kit further comprises other containers comprising one or more of the following: wash reagents, dilution reagents, proteolysis stopping reagents and control proteins with known digestion patterns and instructions for use of the kit.

In detail, a compartmentalized kit includes any kit in which reagents are contained in separated containers. Such containers include glass or plastic containers or strips of plastic or paper. Such containers allow the efficient transfer of reagents from one compartment to another compartment such that the samples and reagents are not cross-contaminated and the agents or solutions of each container can be added in a quantitative fashion from one compartment or another. Such containers will include a container which will accept the microtiter plate, a container which contains wash reagents and proteolysis stopping reagents (eg. acetic acid).

In an alternative embodiment, the kit will include the materials to prepare a device of the present invention, which would therefore, include proteolytic enzymes, blocking reagents and buffer materials. One skilled in the art will readily recognize that the proteolysis device of the present invention can readily be incorporated into one of the established kit formats which are well known in the art.

The following non-limiting examples are illustrative of the present invention:

EXAMPLES

Example 1
General Experimental Protocol for Immobilizing Proteases on Microtiter Plates In this example, four proteolytic enzymes are immobilized on a microtiter plate.

Reagents

The reagents were prepared as follows. A buffer solution of TBS, 50 mM Tris pH 8.0, 150 mM NaCl is prepared for use with the remaining solutions. A solution of TBS, 0.01% beta-octa-glucoside is prepared as a blocking buffer. The following proteases are prepared: Chymotrypsin, 0.5 mg/ml (in TBS); Trypsin, 0.5 mg/ml (in TBS); Papain, 0.5 mg/ml (in TBS); and Proteinase K, 0.5 mg/ml (in TBS). The protein to be digested is prepared at 65 µg/ml (diluted in TBS).

Preparation of Immobilized Protease Plate

In this example of device preparation, Nunclon surface 96 well microtiter plates are used. The proteases are immobilized onto the plates by aliquotting 45 µl TBS into each well. Six wells are used for each protease to generate a series for each protease, each series operating at decreasing concentrations across the wells by adding 5 µl of protease stock solution to the first well, 2.5 µl to the second well, etc. The serial dilution of the wells yield final concentrations of proteases of 50 µg/ml, 25 µg/ml, 5 µg/ml, 2.5 µg/ml, and 0.5 µg/ml. The last well is left for protein only. The plate is covered and placed in a sealable bag with a wet paper towel. The resulting plate is incubated overnight at 4° C.

Blocking of Non-specific Sites on Microtiter Plate

The protease solution is removed from the wells by flicking the plate a few times while inverted. The wells are washed once with blocking buffer (100µl) and the excess solution is removed. 100 µl of blocking buffer is added and incubate for 30 minutes at 4° C. The blocking buffer is removed and the wells are washed once (100 µl) with TBS and the excess TBS is removed. The plates are now ready for use or can be lyophilized and stored at −20° C. until needed.

Digestion of an Protein by an Immobilized Protease

30 µl of the protein solution of interest is added to each well. The resulting plate is then incubated at room temperature for 2–4 hours.

Analysis of Proteolytically Digested Protein

If the protein fragments are to be separated and analyzed by Mass Spectrometry, it is necessary to remove a sample of a proteolytically digested protein (5–10 µl) and stop the proteolysis by adding acetic acid to the sample until a final concentration of 1% is reached.

If the protein fragments are to be separated and analyzed by SDS PAGE Gel Electrophoresis, the proteolysis of protein is stopped by adding 5× protein loading dye to each well. The sample in each well is heated to approximately 90° C. for approximately 5 minutes. 20–25 µl of the sample is loaded onto a SDS PAGE gradient gel (5–18%), and run under electrophoresis followed by a Cornmassie stain to visualize the protein fragments.

Example II

Comparison of Immobilized Protease Digestion to Solution Protease Digestion

Figure 2:
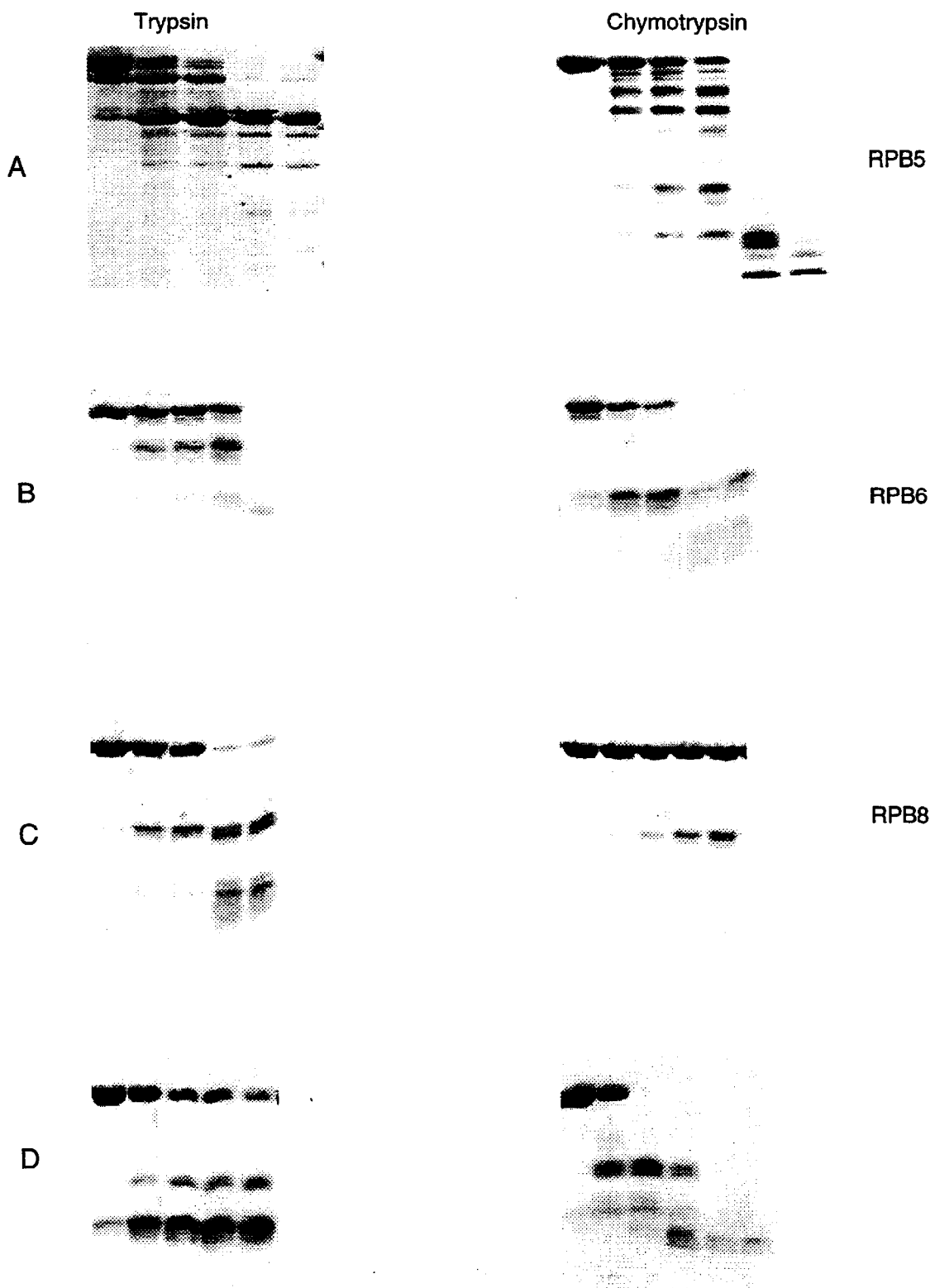
FIG. 2 shows the PAGE results of samples of limited digestion of various proteins in microtitre plates by trypsin and chymotrypsin where A represents the results with RNA polymerase B5; B is RNA polymerase B6; C is RNA polymerase B8; and D is a bacterial protein parB.

The protease plates were used to digest five different proteins whose proteolytic digestion pattern in solution was already known. The pattern of digestion for the immobilized proteases mimicked the solution digestion pattern. Thus, we have shown that the immobilized proteases plates could be used to identify stable domains of several different proteins. Shown in FIG. 1 is an example of a limited digestion of the transcription factor TFIIS from the yeast, *Saccharomyces cerevisiae*. The five lanes shown correspond to the concentration of proteases used (as discussed above in Example I). FIG. 2 illustrates results of digestion on immobilized protease plates of RNA polymerase B5 (see A); RNA polymerase B6 (B); RNA polymerase B8 (C); and D is a bacterial protein parB. Each of these four proteins were digestd by trypsin (panels on the left) and chymotrypsin (panels on the right). These digests compare favourably with similar digests in solution (data not shown).

Example III
Limited Proteolysis

Four different proteases, trypsin, chymotrypsin, papain and proteinase K (Sigma) were immobilized on plastic 96-well microtitre plates (Nuclon) in the following manner. The protease stocks were made 0.5 mg/ml in TBS (50 mM Tris pH 8, 150 mM NaCl). A serial dilution of each protease was prepared to final concentrations of 50 µg/ml, 25 µg/ml, 5 µg/ml, 2.5 µg/ml and 0.5 µg/ml in TBS. 50 µl of each dilution was applied to different wells in a row of the microtitre plate. The plate with the arrayed protease dilutions was then incubated overnight at 4° C. in a sealed bag containing a wet paper towel.

The protease solution was then removed and the wells washed with 100 µl of blocking buffer (TBS, 0.01% beta-octyl glucoside). The first wash was discarded and the non-specific binding sites on the microtitre wells were blocked with an additional 30 minute incubation at 4° C. with an additional 100 µl of blocking buffer.

30 µl of a solution of yeast TFIIS (65 µg/ml) was incubated in each of the protease-coated wells for 2–4 hours at room temperature. 5 µl of the protein solution was then made to 2% Sodium dodecyl sulphate, 25% glycerol, 0.1 M Tris-Hel (pH 8.0) and resolved by gel electrophoresis. The results from a typical digestion (chymotrypsin) are shown in FIG. 1. The individual proteolytic products were purified either by reverse-phase liquid chromatography or by elution from the gel slice and were analyzed by matrix-assisted desorption time-of-flight mass spectrometry. The fragments corresponded to known domains of the yeast TFIIS (Proc. Nat. Acad. Sci. U.S.A. 93:10604–10608, 1996).

Stability

Experiments with plates containing immobilized proteases lyophilized and stored at 4 degrees celcius for up to one week demonstrated results similar to those freshly prepared (data not shown).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. An apparatus for degradation of a protein, said apparatus comprising a plurality of compartments, each compartment containing a quantity of a protease immobilized on a surface in each compartment wherein at least two compartments contain different concentrations of said protease.

2. An apparatus according to claim 1 wherein each compartment containing a quantity of said protease contains a concentration of said protease distinct from the concentration of said protease in every other compartment.

3. An apparatus according to claim 1 wherein at least three concentrations of protease are in said compartments.

4. An apparatus according to claim 3 wherein said plurality of compartments forms a matrix in a linear format with at least three increasing concentrations of protease in said compartments.

5. An apparatus according to claim 1 wherein said matrix contains more than one protease.

6. An apparatus according to claim 5 wherein said matrix is in a two-dimensional format wherein: (i) distinct concentrations of each protease are aligned in increasing concentration, along a first axis or concentration axis; and (ii) different proteases are aligned along a second axis that is perpendicular to the first axis.

7. An apparatus according to claim 1 wherein said protease is selected from the group consisting of aminopeptidase M; bromelain; carboxypeptidase A, B and Y; chymopapain; chymotrypsin; clostripain; collagenase; elastase; endoproteinase Arg-C, Glu-C and LysC; Factor Xa; ficin; Gelatinase; kallikrein; metalloendopeptinidase; papain; pepsin; plasmin; plasminogen; peptidase; pronase; proteinase A; proteinase K; subsilisin; thermolysin; thrombin; and trypsin.

8. An apparatus according to claim 7 wherein the proteases are trypsin, chymotrypsin, proteinase K or papain.

9. An apparatus according to claim 8 wherein the concentrations of each of the proteases along the first axis in each case is from about 50 µg/mL to about 0.5 µg/mL.

10. An apparatus according to claim 9 wherein the concentration for each of the proteases is about 50 µg/mL in one container of a concentration axis; about 25 µg/mL in a second container of the concentration axis; about 5 µg/mL in a third container of the concentration axis; about 2.5 µg/mL in a fourth container of the concentration axis; about 0.51 µg/mL in a fifth container of the concentration axis; about 0 µg/mL in a sixth container of the concentration axis.

11. An apparatus according to claim 1 wherein the surface upon which said protease is immobilized has been treated with a blocker of surface interaction.

12. An apparatus according to claim 11 wherein the blocker is selected from the group consisting of BSA and beta-octyl glucoside.

13. An apparatus according to claim 1 wherein the surface to which said protease is immobilized is selected from the group consisting of an organic support of material selected from the group consisting of polyesters, polyamides, polyacrylates, polymethacrylates, polyacrylamides, poly (acrylic acid)m, poly(methacrylic acid); poly(galacturonic acid); poly(aspartic acid); ethylene-maleic anhydride copolymers; polyolefins; cellulose; cellulose derivatives; agarose gels; dextran gels and derivatives thereof, polysaccharides; polypeptides; collagen; and an inorganic support material selected from the group consisting of siliceous and nonsiliceous metal oxides.

14. An apparatus according to claim 1 wherein the apparatus may be prepared and stored prior to use.

15. An apparatus according to claim 1 wherein said apparatus is a microtitre plate.

16. An apparatus for degradation of a protein, said apparatus comprising a plurality of compartments, each compartment containing a quantity of a protease in solution in each compartment wherein at least two compartments contain different concentrations of said protease.

17. The apparatus of claim 16, wherein said plurality of compartments forms a matrix in a linear format comprising (i) at least three increasing concentrations of protease in said compartments along a first axis, and (ii) at least two different proteases in said compartments along the second axis that is perpendicular to the first axis.

* * * * *